US006984605B2

(12) United States Patent
Hope et al.

(10) Patent No.: US 6,984,605 B2
(45) Date of Patent: Jan. 10, 2006

(54) METHOD FOR MANUFACTURING IONIC LIQUID CATALYSTS

(75) Inventors: Kenneth D. Hope, Kingwood, TX (US); Donald A. Stern, Kingwood, TX (US); Donald W. Twomey, Kingwood, TX (US)

(73) Assignee: Chevron Phillips Chemical Company, LP, The Woodlands, TX (US)

( * ) Notice: Subject to any disclaimer, the term of this patent is extended or adjusted under 35 U.S.C. 154(b) by 158 days.

(21) Appl. No.: 10/420,182

(22) Filed: Apr. 22, 2003

(65) Prior Publication Data

US 2004/0005985 A1 Jan. 8, 2004

Related U.S. Application Data

(60) Provisional application No. 60/374,529, filed on Apr. 22, 2002.

(51) Int. Cl.
*B01J 31/00* (2006.01)
(52) U.S. Cl. ............... 502/164; 502/162; 502/169; 502/167
(58) Field of Classification Search .......... 502/162, 502/164, 169
See application file for complete search history.

(56) References Cited

U.S. PATENT DOCUMENTS

| 2,405,950 | A | 8/1946 | Hanford |
| 4,827,064 | A | 5/1989 | Wu ............... 585/10 |
| 5,087,782 | A | 2/1992 | Pelrine ............ 585/417 |
| 5,196,574 | A | 3/1993 | Kocal |
| 5,304,615 | A | 4/1994 | Ambler ............ 526/189 |
| 5,386,072 | A | 1/1995 | Cozzi et al. |
| 5,731,101 | A | 3/1998 | Sherif ............ 429/102 |
| 5,824,832 | A | 10/1998 | Sherif ............ 585/455 |
| 5,891,830 | A | 4/1999 | Koltermann ........ 308/136 |
| 6,087,307 | A | 7/2000 | Kaminski ......... 508/223 |
| 6,107,374 | A | 8/2000 | Stevens et al. |
| 6,395,948 | B1 | 5/2002 | Hope ............ 585/510 |
| 2002/0128532 | A1 | 9/2002 | Hope ............ 585/521 |
| 2003/0085156 | A1 | 5/2003 | Schoonover |
| 2004/0005985 | A1 | 1/2004 | Hope et al. |
| 2004/0030075 | A1 | 2/2004 | Hope et al. |

FOREIGN PATENT DOCUMENTS

| EP | 0791643 | 8/1997 |
| WO | WO 88/06576 A1 | 9/1988 |
| WO | WO 95/21871 | 8/1995 |
| WO | WO 95/21872 | 8/1995 |
| WO | WO 98/50153 A1 | 11/1998 |
| WO | WO 99/38938 | 8/1999 |

(Continued)

OTHER PUBLICATIONS

Communication Relating to the Results of the Partial International Search, PCT/US 03/12823; Sep. 15, 2003; 2 pages.

(Continued)

*Primary Examiner*—J. A. Lorengo
*Assistant Examiner*—J. Pasterczyk
(74) *Attorney, Agent, or Firm*—Conley Rose, P.C.; Rodney B. Carroll; Joe D. Hulett

(57) ABSTRACT

A method for manufacturing ionic liquid compositions by use of a two-step process which includes the contacting, under first reaction conditions, an amine compound with a hydrogen halide that is preferably in the gaseous form to provide a first reaction mixture. The first reaction mixture is then contacted, under second reaction conditions, with a metal halide compound to form the ionic liquid end-product.

25 Claims, 1 Drawing Sheet

FOREIGN PATENT DOCUMENTS

| WO | WO 00/32658 A1 | 6/2000 |
|----|----------------|--------|
| WO | WO 00/41809 | 7/2000 |
| WO | WO 01/64622 | 9/2001 |
| WO | WO 03/089390 A2 | 10/2003 |

OTHER PUBLICATIONS

Wasserscheid P. et al.; "Ionic Liquids—New Solutions for Transition Metal Catalysis"; Ange Chem. International Edition; vol. 39, Oct. 27, 2000; pp. 3772-3789.

International Search Report and Written Opinion of the International Searching Authority, PCT/US2004/036188, Feb. 23, 2005, 9 pgs.

Schubert, H., "Mechanical Emulsification—New Developments and Trends," Aiche National Meeting, Nov. 12, 2000, XP001160577, 15 pgs.

International Search Report and Written Opinion of the International Searching Authority, PCT/US2004/036410, Feb. 21, 2005, 7 pgs.

International Search Report, PCT/US 03/12821, Jan. 29, 2004, 7 pgs.

Written Opinion of the International Preliminary Examining Authority, PCT/US 03/12821, Feb. 18, 2004, 6 pgs.

International Search Report, PCT/US 03/12823, Dec. 17, 2003, 5 pgs.

Written Opinion of the International Preliminary Examining Authority, PCT/US 03/12823, Jul. 26, 2003, 6 pgs.

International Search Report, PCT/US 03/04838, Jun. 12, 2003, 4 pgs.

Written Opinion of the International Preliminary Examining Authority, PCT/US 03/04838, Apr. 8, 2004, 6 pgs.

U.S. Appl. No. 10/900,221, filed Jul. 27, 2004, Specification and Drawings (Figures 1-5.), 28 pgs.

METHOD FOR MANUFACTURING IONIC LIQUID CATALYSTS

This application claims the benefit of and priority to provisional U.S. Patent Application No. 60/374,529, filed Apr. 22, 2002 and entitled "Method for Manufacturing Ionic Liquid Catalysts." This application is related to U.S. patent application Ser. No. 10/420,261 filed on Apr. 22, 2003 and entitled "Method for Manufacturing High Viscosity Polyalphaolefins Using Ionic Liquid Catalysts." Each of the above-listed applications is hereby incorporated herein by reference in its entirety for all purposes.

FIELD OF THE INVENTION

The present invention relates to a process for manufacturing ionic liquid compositions that are useful for catalyzing certain reactions including, for example, the oligomerization of alpha olefins, and for other purposes. Ionic liquid compositions include, for example, ionic liquids, ionic liquid catalysts, and molten salts.

BACKGROUND OF THE INVENTION

Certain low temperature ionic liquids are known to have properties that make them suitable for use as catalysts. U.S. Pat. No. 5,731,101 discloses certain low temperature molten ionic liquid compositions that are mixtures of a metal halide and an alkyl-containing amine hydrohalide salt made by combining solids of each component and forming a liquid of the mixture.

Considering the usefulness of low temperature ionic liquids as catalysts, it is desirable to have a commercially economical method for manufacturing commercial quantities of such low temperature ionic liquids. It is, therefore, an object of this invention to provide such a manufacturing method.

SUMMARY OF INVENTION

This invention relates to a process for manufacturing liquid ionic compositions that are useful as a catalyst. The process is a two step process which includes contacting under first reaction conditions an alkylamine with a hydrogen halide that is preferably in the gaseous form to thereby form a first reaction mixture. The first reaction mixture is contacted under second reaction conditions with a metal halide compound to thereby form the ionic liquid end-product.

DETAILED DESCRIPTION

Figure 1:
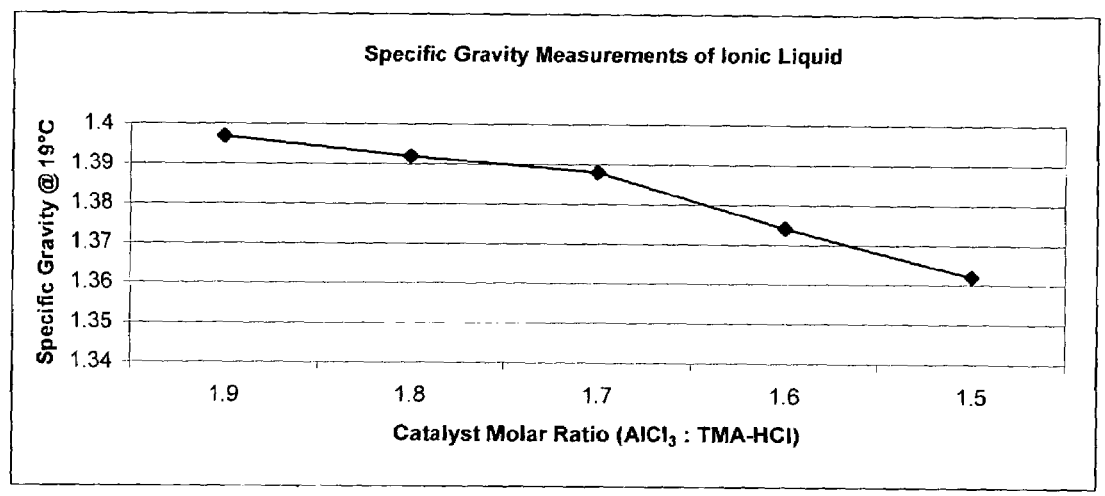
FIG. 1 is a graph of metal halide to alkylamine salt ratio versus specific gravity for an ionic liquid catalyst comprising aluminum trichloride and a salt of trimethylamine and hydrogen chloride.

The ionic liquid composition made by the novel processes or methods described herein are complexes of two components that form low temperature molten compositions. One component is a metal halide and the other component is an alkyl-containing amine hydrohalide salt. It is preferred for the ionic liquid compositions produced by the inventive processes to be in a liquid form at temperatures below about 120° F. at standard pressure. It is more preferred, however, for the ionic liquid compositions to be a liquid below about 100° F. and, more preferably, below 80° F. at standard pressure.

As noted above, U.S. Pat. No. 5,731,101 describes a method of making the ionic liquid compositions by mixing together solids of the two components and heating, if necessary, until the mixture becomes a liquid. The inventive method described herein is a two-step process that is significantly different from the single step process of mixing two solid components described in U.S. Pat. No. 5,731,101. The ionic liquid composition is produced by first contacting under effective first reaction conditions an alkyl amine with a hydrogen halide that is preferably in a gaseous state to thereby form a first reaction mixture. The first reaction mixture is then contacted under effective second reaction conditions with a metal halide to form the ionic liquid composition.

The metal halides useful in this invention are those compounds which can form the ionic liquid complexes that are in liquid form at the temperatures noted above when combined with an alkyl-containing amine hydrohalide salt. Preferred metal halides are covalently bonded metal halides. Possible suitable metals which can be selected for use herein include those from Groups VIII, IB, IIB, and IIIA of the Periodic Table of the Elements, CAS version. More specifically, the metal of the metal halides can be selected from the group consisting of aluminum, gallium, iron, copper, zinc, and indium. Preferred among these metals are aluminum and gallium, and most preferred is aluminum. Preferred metal halides include those selected from the group consisting of aluminum halide, alkyl aluminum halide, gallium halide, and alkyl gallium halide, of which, especially preferred are aluminum halide or alkyl aluminum halide. The most preferred metal halide as a reactant for use in the inventive process is aluminum trichloride.

The alkyl-containing amine hydrohalide salts useful in this invention include monoamines, diamines, triamines and cyclic amines, all of which include one or more alkyl group and a hydrohalide anion. The term alkyl is intended to cover straight and branched alkyl groups having from 1 to 9 carbon atoms. The preferred alkyl-containing amine hydrohalide salts useful in this invention have at least one alkyl substituent and can contain as many as three alkyl substituents. They are distinguishable from quaternary ammonium salts which have all four of their substituent positions occupied by hydrocarbyl groups. The preferred compounds that are contemplated herein have the generic formula $R_3N \cdot HX$, where at least one of the "R" groups is alkyl, preferably alkyl of from one to eight carbon atoms (preferably, lower alkyl of from one to four carbon atoms) and X is halogen, preferably chloride. If each of the three R groups is designated $R_1$, $R_2$ and $R_3$, respectively, the following possibilities exist in certain embodiments: each of $R_1$–$R_3$ can be lower alkyl optionally interrupted with nitrogen or oxygen or substituted with aryl; $R_1$ and $R_2$ can form a ring with $R_3$ being as previously described for $R_1$; $R_2$ and $R_3$ can either be hydrogen with $R_1$ being as previously described; or $R_1$, $R_2$ and $R_3$ can form a bicyclic ring. Most preferably, these groups are methyl or ethyl groups. If desired the di- and tri-alkyl species can be used. One or two of the R groups can be aryl, but this is not preferred. The alkyl groups, and aryl, if present, can be substituted with other groups, such as a halogen. Phenyl and benzyl are representative examples of possible aryl groups to select. However, such further substitution may undesirably increase the viscosity of the melt. Therefore, it is highly desirable that the alkyl groups, and aryl, if present, be comprised of carbon and hydrogen groups, exclusively. Such short chains are preferred because they form the least viscous or the most conductive melts. Mixtures of these alkyl-containing amine hydrohalide salts can be used.

The most preferred alkyl containing amine hydrohalide salt are those compounds where the R groups are either hydrogen or an alkyl group having 1 to 4 carbon atoms, and the hydrohalide is hydrogen chloride, an example of which is trimethylamine hydrochloride.

The inventive two step process is advantageous in that it provides a means for economically manufacturing commercial quantities of ionic liquid compositions that can suitably be used as catalysts. The first step of the inventive process requires the introduction into a reaction zone a first diluent and an alkylamine that are preferably liquid under the reaction conditions of the first step of the inventive process. The first diluent and liquid alkylamine are intimately mixed together either prior to their introduction into the reaction zone or while contained within the reaction zone, but, in any event, for the best performance of the first reaction step of the inventive process, it is preferred for the first diluent and liquid alkylamine to be a substantially homogenous mixture prior to introduction of hydrogen halide fluid into the reaction zone of the first reaction step of the process.

Following or simultaneously with the introduction of the first diluent and liquid alkylamine into the first reaction zone, a fluid that comprises hydrogen halide, preferably, hydrogen chloride, is introduced at a controlled rate into the first reaction zone and contacted with the liquid alkylamine therein. It is preferred for at least a portion of hydrogen halide introduced into the first reaction zone to be in the gaseous state. It is most preferred for the introduced hydrogen halide to be substantially in the gaseous state.

The temperature within the first reaction zone during the introduction of the hydrogen halide fluid is maintained within a temperature range of from about −20° F. to about 60° F., preferably from about 0° F. to about 50° F. and, most preferably from 5° F. to 40° F. The pressure maintained in the first reaction zone during the first reaction step should generally be maintained to at least about atmospheric, preferably, the pressure is controlled to within the range of from about 20 psia to about 150 psia and, most preferably, the pressure is in the range of from 25 psia to 100 psia. The pressure is controlled by any suitable means known in the art. One such possible means is by the introduction or removal of an inert gas, such as nitrogen, into the vapor space of the first reaction zone as is required to maintain the desired pressure therein.

The reaction between the alkylamine and hydrogen halide is exothermic and, therefore, a means is required for removing the heat of reaction from the first reaction zone during the contacting of the hydrogen halide with the alkylamine and maintaining the temperature within a desired temperature range. Controlling the reaction temperature within the desired temperature range is a critical aspect of the inventive process and the rate of introduction of the hydrogen halide fluid is controlled in a manner so as to assist in maintaining the temperature within the first reaction zone within the desired range during the contacting of the hydrogen halide and alkyl amine.

The first diluent used in the first reaction step of the inventive process can be any compound which can serve as a suitable solvent for the alkylamine, is liquid under the reaction conditions of the first reaction step, and is inert to the alkylamine, hydrogen halide and metal halide feedstocks of the inventive process. Generally, alkanes having from four to twelve carbon atoms can be used. Preferably, alkane compounds that can suitably be used as a first diluent include hexanes, such as cyclohexane, and heptanes. The most preferred materials for use as the first diluent include polyalphaolefins that can be dimers, trimers, oligomers or polymers of an alpha olefin or a mixture of dimers, trimers, oligomers or polymers of alpha olefins all of which should suitably serve as a solvent for the alkylamine and are liquid under the reaction conditions of the first reaction step. The weight ratio of first diluent to alkylamine should be in the range of from about 500:1 to about 1:1. Preferably, the weight ratio of first diluent to alkylamine is in the range of from about 20:1 to about 1:1 and, most preferably, from 15:1 to 5:1.

It is desirable for a sufficient quantity of hydrogen halide to be introduced into the first reaction zone to convert a substantial portion of the alkylamine to the salt of the alkylamine and hydrogen halide which forms as a solid slurried within the diluent thereby forming the first reaction mixture. Typically, the amount of hydrogen halide introduced into the first reaction zone is such as to provide a molar ratio of the alkylamine to hydrogen halide to be in the range of from about 0.1:1 to about 5:1 and, preferably, from about 0.5:1 to about 2:1. Most preferably, the amount of hydrogen halide introduced into the first reaction zone provides for a molar ratio of alkylamine to hydrogen halide of from 0.8:1 to 1.2:1.

Upon the substantial completion of the reaction of the first reaction step, the first reaction mixture is contacted, or mixed, under second reaction conditions and within a reaction zone, with a metal halide that is preferably aluminum trichloride to thereby form a second reaction product that comprises the ionic liquid end-product. The second step may be conducted in the same reaction zone as that of the first reaction step or, alternatively and preferably, the first reaction product comprising the solid alkylamine hydrogen halide salt slurried within the first diluent can be transferred into a separate second reaction zone wherein the second step of the inventive process is conducted.

In conducting the second step of the process, the metal halide is introduced into or mixed with the first reaction mixture. The metal halide shall be in the form of either a dry solid or a slurry of a second diluent and solid metal halide. It is preferred, however, to add the metal halide to the first reaction mixture in the form of a dry solid. The dry solid metal halide is dry in the sense that it contains very little water, preferably having less than 1 weight percent, and, most preferably, less than 0.1 weight percent, water concentration. While the dry solid metal halide can be in any form, it is preferred for it to be a finely divided powder which will enhance its ability to react with the reaction product of the first reaction mixture to form the ionic liquid catalyst.

The second diluent used to form the slurry of solid metal halide can be the same material as is used for the first diluent; provided, it suitably provides a slurry, is liquid under the reaction conditions of the inventive process, and is inert to the reactants of the inventive process. Generally, alkanes having from four to twelve carbon atoms can be used. Preferably, the alkane compounds that can suitably be used as the second diluent are hexanes, such as cyclohexane, and heptanes. The most preferred materials for use as the second diluent include polyalphaolefins that can be any dimer, trimer, oligomer or polymer of an alpha olefin all of which should suitably form the desired slurry and is liquid under the reaction conditions of the second reaction step. The weight ratio of second diluent to metal halide solid should be in the range of from about 100:1 to about 1:1.

Preferably, the weight ratio of second diluent to metal halide in the slurry is in the range of from about 10:1 to about 1:1 and, most preferably, from 3:1 to 1:1.

In the second reaction step, a sufficient amount of metal halide is contacted with the salt of alkylamine and hydrohalide produced in the first reaction step to convert at least a portion, preferably a substantial portion, thereof to the ionic liquid end-product. As noted above, the metal halide can be introduced into, or contacted with, the product resulting from the first reaction step either as a solid that is preferably in powdered form or as a component of a slurry of the second diluent and the metal halide. Typically, the molar ratio of metal halide and alkylamine salt combined together in the second reaction step of the inventive process is in the range of from about 0.1:1 to about 2:1, but, preferably, the range is from about 0.5:1 to about 2:1. The most preferred range for the molar ratio of metal halide and alkylamine salt combined together in the second reaction step is from 1:1 to 2:1; particularly, if it is desired to manufacture an acidic catalyst. The use of a molar ratio at or near 1:1 will tend to provide an ionic liquid product that is a neutral ionic liquid. At the upper end of the range for the molar ratio, precipitation tends to occur. As the molar ratio of metal halide and alkylamine salt decreases further, the resulting ionic liquid product formed tends to move from being a neutral ionic liquid to a basic ionic liquid, both of which can have uses other than as ionic liquid catalysts.

The temperature maintained during the second reaction step should be in the range of from about 40° F. to about 250° F. Preferably, however, the temperature of the second reaction step is maintained in the range of from about 50° F. to about 225° F. and, most preferably, the temperature range is from 70° F. to 200° F. While the temperature conditions of the second reaction step are important to the operation of the inventive process, the reaction pressure of the second reaction step is not as important. But, the pressure maintained during the second reaction step should generally be in the range of from slightly below atmospheric pressure to about 150 psia and, preferably, from atmospheric pressure to 50 psia.

Upon completion of the second step of the inventive process, the formed ionic liquid composition may be separated from the diluents by any suitable means know in the art, for example, by phase separation means.

Also disclosed herein is a method for determining the composition of an ionic liquid comprising (a) measuring the specific gravity and molar composition of a plurality of samples of the ionic liquid; (b) correlating the specific gravity to the molar composition of the plurality of samples; (c) measuring the specific gravity of an additional sample of the ionic liquid; and (d) determining the molar ratio of the additional sample comparing the specific gravity of the additional sample from step (c) to the correlation from step (b).

In an embodiment, the composition of an ionic liquid catalyst is determined via a correlation to the specific gravity of the ionic liquid catalyst. Samples of a given ionic liquid catalyst are taken from a plurality of different manufacturing lots or batches and analyzed to determine the specific gravity of each batch and the molar ratio of a metal halide to a salt of an alkylamine and hydrogen halide. The specific gravity is determined by a hydrometer reading at 19° C. Known molar ratios from 1.5 to 1.9 were prepared and the specific gravity at 19° C. was measured. In alternative embodiments, the molar ratio of the molar ratio of a metal halide to a salt of an alkylamine and hydrogen halide may be from about 0.1 to about 3.0, alternatively from about 0.1 to about 2.5, alternatively from about 0.1 to about 2, alternatively from about 0.5 to about 2, and alternatively from about 1 to about 2. The molar ratio and specific gravity data are plotted on a graph. To determine the composition of a sample of a subsequent batch of the given liquid ionic catalyst, the specific gravity of the sample is determined as described previously, and the specific gravity is correlated to molar ratio using the curve. FIG. 1 is a graph of molar ratio versus specific gravity for an ionic liquid catalyst comprising aluminum trichloride ($AlCl_3$) and a salt of trimethylamine (TMA) and hydrogen chloride (HCl). The data plotted in FIG. 1 is listed in Table 1. Such an analytical process is useful, for example, for quality control of ionic liquid catalyst batches, and such a process has an advantage in that the specific gravity determination via hydrometer tube is relatively simple and quick in comparison to the molar ratio analysis via elemental analysis.

TABLE 1

| Molar ratio $AlCl_3$:TMA-HCl | Specific gravity at 19° C. |
| --- | --- |
| 1.9 | 1.397 |
| 1.8 | 1.392 |
| 1.7 | 1.388 |
| 1.6 | 1.374 |
| 1.5 | 1.362 |

The following Examples are provided only to illustrate the invention, and they should not be considered as a limitation thereof.

EXAMPLE 1

This Example 1 illustrates the process for manufacturing an ionic liquid that is useful as a catalyst by using as the reactants trimethylamine, gaseous hydrogen chloride, and aluminum trichloride in the novel two-step process described above.

550 lbs of Synfluid® PAO 2 were added into a 500 gallon glass-lined stirred tank reactor. The reactor was then purged and pressurized with nitrogen to 5 psig while cooling the contents to 20° F. While maintaining the temperature below 22° F., 52 lbs of trimethylamine were added via liquid addition. This was done stepwise to prevent overpressure of the reactor. The conditions of the reactor resulted in 7 psig and 22° F.

The addition of the 33 lbs of gaseous hydrogen chloride was accomplished by slowly pressurizing the reactor. This was done to maintain a temperature below 22° F. and a final pressure below 8 psig.

In a second glass-lined stirred tank reactor 550 lbs of Synfluid PAO 2 was added and purged with nitrogen. 200 lbs of aluminum chloride in powdered form was added stepwise under stirring to generate a slurry.

The two reaction mixtures were combined in a single reactor under stirring. The reactor contents were heated to 120° F. Upon heating an exotherm occurred and a drop in the reaction temperature indicated the end of the reaction. The stirring was shut off to allow separation of the ionic liquid catalyst and the diluent. Sampling from the lower phase showed a reddish brown liquid with a specific gravity 1.378 at 24° C. This resulted in approximately 27 gallons of ionic liquid.

EXAMPLE 2

This Example 2 illustrates the one step process for manufacturing an ionic liquid in which the alkylamine salt is combined with the metal halide in a single step.

A slurry of cyclohexane and of solid trimethylamine hydrochloride and a slurry cyclohexane and aluminum chloride were used to make the ionic liquid product. The cyclohexane slurries were prepared in a double-barreled addition funnel. The reagent weights were 1.01 g trimethylamine hydrochloride and 2.47 g $AlCl_3$. Anhydrous cyclohexane was added in excess to each side of the double-barreled addition funnel. Cyclohexane was added in excess and not measured; because, it could be easily separated from the catalyst mixture. The trimethylamine hydrochloride/cyclohexane slurry and the $AlCl_3$/cyclohexane slurry were added simultaneously to a receiving beaker. No reaction was apparent at first. A semi-viscous, yellow liquid formed following swirling of the mixture by hand. Some solids remained, even after 25 minutes of mixing. The material could be filtered or decanted prior to using as a catalyst.

One disadvantage of the single step manufacturing method illustrated in this Example 2 over the two-step process illustrated in Example 1 is the difficulty in handling the alkylamine hydrohalide salt compared to handling an alkylamine. The two-step process provides for easier handling of the reagents and is a more commercially viable manufacturing process as compared to a single step process.

EXAMPLE 3

This Example 3 demonstrates the ability to manufacture the ionic liquid product using the two step process but without using a slurry of the metal halide, i.e. using the metal halide in solid form, in the second step.

A procedure for preparing the ionic liquid catalyst was repeated as in Example 1 except the aluminum chloride was introduced as a solid via a solids addition funnel rather than as a slurry. An ionic liquid product was produced.

The preceding Examples are presented only for the purpose of illustrating the invention, thus, they should not be construed in a limiting sense. The scope of protection sought is set forth in the following claims.

That which is claimed is:

1. A process comprising:
   contacting under first reaction conditions an alkylamine with a hydrogen halide gas to form a first reaction mixture; and
   thereafter, contacting under second reaction conditions said first reaction mixture with metal halide to form an ionic liquid catalyst, wherein the first reaction conditions comprise a first reaction temperature maintained within the range of from about −20° F. to about 60° F.

2. A process in accordance with claim 1 wherein the quantity of hydrogen halide contacted with the alkylamine is sufficient to convert a substantial portion of the alkylamine to the salt of the alkylamine and hydrogen halide and to thereby provide said first reaction mixture comprising a solid.

3. A process in accordance with claim 2 wherein the alkylamine is a compound having the generic formula, $R_3N$, wherein each R group may be independently selected as hydrogen or an alkyl group having from 1 to 4 carbon atoms, provided that all three R groups are not hydrogen.

4. A process in accordance with claim 3 wherein the hydrogen halide is hydrogen chloride and the alkylamine is trimethylamine.

5. A process in accordance with claim 4 wherein the second reaction conditions comprise a second reaction temperature maintained within the range of from about 40° F. to about 250° F.

6. A process in accordance with claim 5 wherein the metal of the metal halide is selected from the group consisting of aluminum, gallium, iron, copper, zinc, and indium.

7. A process in accordance with claim 6 wherein the amount of hydrogen halide contacted with the alkylamine is such as to provide a molar ratio of the alkylamine to hydrogen halide in the range from about 0.1:1 to about 5:1.

8. A process in accordance with claim 7 wherein said first reaction mixture comprises a salt of the alkylamine and hydrogen halide and wherein the amount of metal halide contacted with said first reaction mixture is such as to provide a molar ratio of metal halide to alkylamine salt of said first reaction mixture in the range from about 0.1:1 to about 2:1.

9. A process for manufacturing an ionic liquid catalyst, said process comprising the steps of:
   forming a first reaction mixture by mixing with an alkylamine a fluid comprising a gaseous hydrogen halide; and
   mixing with said first reaction mixture a material comprising a metal halide to thereby form a second reaction mixture comprising said ionic liquid catalyst, wherein the first reaction conditions comprise a first reaction temperature maintained within the range of from about −20° F. to about 60° F.

10. A process in accordance with claim 9 wherein the quantity of hydrogen halide contacted with the alkylamine is sufficient to convert a substantial portion of the alkylamine to the salt of the alkylamine and hydrogen halide and to thereby provide said first reaction mixture comprising a solid.

11. A process in accordance with claim 9 wherein the alkylamine is a compound having the generic formula, $R_3N$, wherein each R group may be independently selected as hydrogen or an alkyl group having from 1 to 4 carbon atoms, provided that all three R groups are not hydrogen.

12. A process in accordance with claim 11 wherein the hydrogen halide is hydrogen chloride and the alkylamine is trimethylamine.

13. A process in accordance with claim 12 wherein the second reaction conditions comprise a second reaction temperature maintained within the range of from about 40° F. to about 250° F.

14. A process in accordance with claim 13 wherein the metal of the metal halide is selected from the group consisting of aluminum, gallium, iron, copper, zinc, and indium.

15. A process in accordance with claim 14 wherein the amount of hydrogen halide contacted with the alkylamine is such as to provide a molar ratio of the alkylamine to hydrogen halide in the range from about 0.1:1 to about 5:1.

16. A process in accordance with claim 15 wherein said first reaction mixture comprises a salt of the alkylamine and hydrogen halide and wherein the amount of metal halide contacted with said first reaction mixture is such as to provide a molar ratio of metal halide to alkylamine salt of said first reaction mixture in the range from about 0.1:1 to about 2:1.

17. A method for manufacturing an ionic liquid catalyst, said method comprising the steps of:
   mixing within a first reaction zone and under first reaction conditions a liquid alkylamine with a first diluent to thereby form a first mixture comprising said first diluent and alkylamine;

introducing a gaseous hydrogen chloride into said first mixture under the first reaction conditions to thereby cause a first reaction thus forming a first reaction product comprising a salt of said alkylamine and hydrogen chloride commingled with said first diluent;

allowing said first reaction to occur; and mixing, under second reaction conditions, a metal halide with said first reaction product, to thereby cause a second reaction thus forming a second reaction product comprising an ionic liquid catalyst, wherein the metal halide is mixed with a second diluent, the second diluent is an alkane that is liquid under the second reaction conditions, and the weight ratio of the second diluent to metal halide is in the range of from about 100:1 to about 1:1.

18. A method as recited in claim 17 wherein the first reaction conditions comprise a temperature which is maintained within a temperature range of from about −20° F. to about 60° F. and a pressure of at least about one atmosphere.

19. A method as recited in claim 18 wherein said first diluent is an alkane that is liquid under the first reaction conditions, and wherein the weight ratio of said first diluent and said liquid alkylamine is in the range of from about 500:1 to about 1:1.

20. A method as recited in claim 19 wherein the amount of hydrogen chloride introduced into said first mixture is such as to provide a sufficient quantity thereof to convert a substantial portion of said liquid alkylamine to said salt of an alkylamine and hydrogen chloride.

21. A method as recited in claim 20 wherein the amount of gaseous hydrogen chloride introduced into said first mixture is such as to provide a molar ratio of said liquid alkylamine to hydrogen chloride in the range of from about 0.1:1 to about 5:1.

22. A method as recited in claim 21 wherein the second reaction conditions are such that the temperature is maintained in the range of from about 40° F. to about 250° F.

23. A method as recited in claim 22 wherein the metal of said metal halide is selected from the group consisting of aluminum, gallium, iron, copper, zinc and indium.

24. A method as recited in claim 23 wherein said liquid alkylamine is an alkylamine having the generic formula, $R_3N$, wherein each R group may be independently selected as hydrogen or an alkyl group having from 1 to 4 carbon atoms, provided that all three R groups are not hydrogen.

25. The method of claim 17 wherein the first diluent, second diluent, or both comprise polyalphaolefins.

* * * * *